United States Patent [19]
Serre

[11] 3,966,923
[45] June 29, 1976

[54] MEDICAMENTS INTENDED FOR THE PREVENTION AND TREATMENT OF ISCHEMIC DISTURBANCES

[75] Inventor: Hubert Serre, Paris, France

[73] Assignee: Pierre Fabre S.A., Paris, France

[22] Filed: Aug. 4, 1975

[21] Appl. No.: 601,303

Related U.S. Application Data

[63] Continuation-in-part of Ser. No. 366,608, June 4, 1973, abandoned.

[30] Foreign Application Priority Data

June 5, 1972 France.............................. 72.20390

[52] U.S. Cl............................. 424/232; 424/258; 424/261; 424/262
[51] Int. Cl.² ...................................... A61K 31/625
[58] Field of Search ............ 424/232, 261, 262, 258

[56] References Cited
UNITED STATES PATENTS 3,629,471   12/1971   Fanchamps et al................. 424/261

OTHER PUBLICATIONS

Chem. Abst.(1), 73–64604Q, (1970).

Chem. Abst.(2), 51–13203b, (1957).

Grollman, Pharmacology & Therapeutics, 6th Ed., 525–545 (1965).

Primary Examiner—Stanley J. Friedman
Attorney, Agent, or Firm—Gordon W. Hueschen

[57] ABSTRACT

The present invention concerns new compositions which are useful as medicaments. These compositions contain vasodilators or vasoregulators and substances which decrease the adhesiveness and aggregability of the blood platelets. They are useful for the prevention and treatment of circulatory insufficiency, whatever the location thereof.

18 Claims, No Drawings

MEDICAMENTS INTENDED FOR THE PREVENTION AND TREATMENT OF ISCHEMIC DISTURBANCES

This application is a continuation-in-part of my prior-filed co-pending application Ser. No. 366,608, filed June 4, 1973, now abandoned, which application claims priority of French application Ser. No. 72,20390, filed June 5, 1972.

The present invention, developed at the Pierre Fabre Research Center, concerns new pharmaceutical compositions which contain on the one hand vasodilators or vasoregulators and on the other hand substances which affect the adhesiveness and aggregability of the blood platelets.

These new medicaments are useful for the prevention and treatment of circulatory insufficiency, whatever the location thereof (peripheral, coronary, cerebral). They may be administered by mouth, rectally or parenterally.

Up to now vasodilators or vasoregulators of more or less elective tropism have been used to treat vascular disturbances the frequency and seriousness of which are known; this is a palliative treatment which is at most preventive but in no case causal.

However, in order truly to counteract the processes responsible for circulatory insufficiency, it is necessary to take into account the role of the blood platelets in their etiology.

The platelets participate, as a matter of fact, both in the formation of atheroma and of thrombosis. The applicant therefore had the idea of systematically combining substances capable of decreasing the adhesiveness and aggregability of platelets with one or more of the following vasotropes:

Raubasine, adrenolytic and sympatholytic alkaloids of ergot (dihydroergotoxin, dihydroergocristine, dehydroergotamine), alkaloids of Vinca minor (in particular vincamine), purine bases and nicotine derivatives in the wide sense of the expression, papaverine, and nitro derivatives.

Certain thrombocytotropic substances were tested; aspirin constitutes the most representative product, but any substance related to aspirin (salts, esters, amides) and having this "aspirin like" action can be combined with a vasodilator or vasoregulator from among those enumerated above. After pharmacological study, some of these combinations have been used in treatment.

The first tests were carried out with acetyl salicylic acid or acetyl salicylate of DMAE as antiaggregants. The toxicity of these combinations (acute and chronic toxicology) and the vasodilatory action were verified on animals, and conventional tests on coagulability were carried out (bleeding time, ADP test, "rolling tubes" method, etc.).

Finally, the applicant found in animals that no harmful interaction between the vasodilators and antiaggregants selected appeared (toxic effect, retained vasodilator action, anti-aggregant power of the combinations).

A potentializing action of the adrenolytic with respect to the salicyl on the platelet adhesiveness-aggregability was observed.

The formulas of the combinations which were the object of the clinical studies are given below by way of illustration and not of limitation:

Example 1
Dragees in accordance with formula:
Raubasine base 4 mg
Aspirin 200 mg
Excipient q.s. for 1 dragee
Dose: 4 to 5 dragees per day Example 2
Dragees in accordance with formula:
Dihydroergocristine methane sulfonate 1 mg
Dimethyl aminoethanol acetyl salicylate 150 mg
Excipient q.s. for 1 dragee
Dose: 3 to 4 dragees per day Example 3
Tablets according to formula:
Dihydroergotoxin methane sulfonate 1 mg
Acetyl salicylic acid 200 mg
Glycine 150 mg
Excipients q.s. for 1 tablet
Dose: 3 to 4 dragees per day Example 4
Lyophilizate according to formula:
Vincamine 10 mg
DMAE acetyl salicylate 200 mg
Sodium methyl p-hydroxy benzoate 2 mg Solvent: sodium chloride solution 5 ml
Dose: 2 to 3 injections intramuscularly per day Example 5
Capsules (delayed-action form) according to formula:
Papaverine (HCl) in microencapsulated form 150 mg
DMAE acetyl salicylate 200 mg
Excipient q.s. for 1 capsule
Dose: 1 capsule in the morning, 1 capsule in the evening before going to bed Example 6
Dragees according to formula:
3 pyridine carbinil theophylline 7 acetate 250 mg
DMAE acetyl salicylate 150 mg
Excipient q.s. for 1 dragee with enteric disintegration
Dose: 3 dragees per day When tested on six groups of 30 patients suffering from cerebral circulatory insufficiency, these combinations proved clearly to be more active (disappearance or spacing of the attacks, improvement in performances and behavior) than the corresponding vasotropes used alone in the same doses. We did not observe any increased allergy to aspirin or hemorrhagic phenomenon.

The present invention concerns medicinal combinations such as described but to which there are added other principles such as vitamins, sedatives and diuretics.

The following combination (Example 7) was tested in 25 patients suffering from angina and the improvement in the therapeutic results as compared with those of the coronary dilator used alone was found again.

Example 7
Trinitrin 3 mg
DMAE acetyl salicylate 150 mg
Excipients q.s. for 1 multi-coat tablet with delayed disintegration From the foregoing Examples, it is clear that the components of the compositions of the present invention can be employed in effective amounts in widely varying proportions by weight, for example: about 1 –

250 parts of vasotrope (a) to about 150 – 200 parts of thrombocytotropic substance (b), in each case in a form useful in medicaments, it being noted that the foregoing Examples 2 and 5 provide proportions of (a) to (b) which are 1 to 150 and 1 to 1.3.

Other effective amounts may be substituted for those given in the foregoing Examples, for example, the amount of dimethylaminoethanol acetyl salicylate (b) in Example 2 together with a pharmaceutically-acceptable dihydroergocristine acid addition salt can obviously be increased to 250 parts of even more, and the number of parts of dimethylaminoethanol acetyl salicylate (b) in Example 5 together with a pharmaceutically-acceptable papaverine acid addition salt can obviously be increased to twenty parts or even more, even up to 250 parts or so. Representative tests have shown, for example, that, with respect to ADP, there is a significant difference between the platelet antiaggregant effect of dimethylaminoethanol acetyl salicylate (SC-1) alone and when combined or administered together with a papaverine acid addition salt in proportions of ten to one by weight, and that, with respect to collagen, there is a significant potentiation of platelet antiaggregant effect between SC-1 alone and when combined or administered together with a papaverine acid addition salt in proportions of ten to one and twenty to one by weight, total inhibition of platelet aggregation being observed at some concentrations at which the individual components alone have no substantial antiaggregant effect. As to a combination or concurrent administration of SC-1 and a dihydroergocristine acid addition salt, tests have demonstrated a platelet antiaggregant effect significantly superior to SC-1 alone at weight proportions as high as 250 to one. Thus, even though the dihydroergocristine has no direct antiaggregant effect by itself, but only adrenalytic action, it apparently significantly potentiates the antiaggregant effect of SC-1 even when present or employed on a weight basis in an amount no greater than about one part to 250. Such potentiations of antiaggregant effect are obviously not predictable from the properties of the individual active ingredients, components, or principles.

Various modifications in the compounds, compositions, and method of the invention will be apparent to one skilled in the art and may be made without departing from the spirit or scope thereof, and it is therefore to be understood that the invention is to be limited only by the scope of the appended claims.

What is claimed is:

1. Pharmaceutical composition useful in the treatment of circulatory insufficiency comprising
   a. a vasotrope compound selected from the group consisting of dihydroergocristine, papaverine, and a pharmaceutically acceptable salt of such vasotrope compound, and
   b. a thrombocytotropic substance selected from the group consisting of dimethylaminoethanol acetyl salicylate and salt forms thereof which are pharmaceutically useful, the combined amount of said compound and said substance being sufficient to inhibit platelet aggregation to an extent greater than the additive effects of the individual components, (a) and (b) being present in amounts so as to provide the components in a proportion of about one part of the vasotrope compound (a) to about one to 250 parts of the thrombocytotropic substance (b).

2. Composition in accord with claim 1 comprising dihydroergocristine acid addition salt as the vasotrope compound (a) and dimethylaminoethanol acetyl salicylate as the thrombocytotropic substance (b).

3. Composition in accord with claim 2 comprising the ingredients (a) and (b) in a proportion of about one part of (a) dihydroergocristine methane sulfonate to about 150 – 250 parts of (b) dimethylaminoethanol acetyl salicylate.

4. Composition in accord with claim 2 comprising the ingredients (a) and (b) in a proportion of about one part of (a) dihydroergocristine methane sulfonate to about 150 parts of (b) dimethylaminoethanol acetyl salicylate.

5. Composition in accord with claim 2 comprising the ingredients (a) and (b) in a proportion of about one part of (a) dihydroergocristine methane sulfonate to about 250 parts of (b) dimethylaminoethanol acetyl salicylate.

6. Composition in accord with claim 1 comprising papaverine acid addition salt as the vasotrope compound (a) and dimethylaminoethanol acetyl salicylate as the thrombocytotropic substance (b).

7. Composition in accord with claim 6 comprising the ingredients (a) and (b) in a proportion of about one part of (a) papaverine hydrochloride to about 1.3 to 20 parts of (b) dimethylaminoethanol acetyl salicylate.

8. Composition in accord with claim 6 comprising the ingredients (a) and (b) in a proportion of about one part of (a) papaverine hydrochloride to about 1.3 parts of (b) dimethylaminoethanol acetyl salicylate.

9. Composition in accord with claim 6 comprising the ingredients (a) and (b) in a proportion of about one part of (a) papaverine hydrochloride to about twenty parts of (b) dimethylaminoethanol acetyl salicylate.

10. A method for the treatment of circulatory insufficiency which comprises administering to a patient subject to circulatory insufficiency an amount effective for alleviation of such condition of a combination of active principles comprising
    a. a vasotrope compound selected from the group consisting of dihydroergocristine, papaverine, and a pharmaceutically acceptable salt of such vasotrope compound, and
    b. a thrombocytotropic substance selected from the group consisting of dimethylaminoethanol acetyl salicylate and salt forms thereof which are pharmaceutically useful, in amounts so as to provide the active principles in a proportion of about one part of the vasotrope compound (a) to about one to 250 parts of the thrombocytotropic substance (b).

11. The method according to claim 10 wherein dihydroergocristine acid addition salt is the vasotrope compound (a) and dimethylaminoethanol acetyl salicylate is the thrombocytotropic substance (b).

12. Method of claim 11, wherein the active ingredients are (a) and (b) in a proportion of about one part of (a) dihydroergocristine methane sulfonate to about 150 – 250 parts of (b) dimethylaminoethanol acetyl salicylate.

13. Method of claim 11, wherein the active ingredients are (a) and (b) in a proportion of about one part of (a) dihydroergocristine methane sulfonate to about 150 parts of (b) dimethylaminoethanol acetyl salicylate.

14. Method of claim 11, wherein the active ingredients are (a) and (b) in a proportion of about one part of (a) dihydroergocristine methane sulfonate to about 250 parts of (b) dimethylaminoethanol acetyl salicylate.

15. The method according to claim 10 wherein papaverine acid addition salt is the vasotrope compound (a) and dimethylaminoethanol acetyl salicylate is the thrombocytotropic substance (b).

16. Method of claim 15, wherein the active ingredients are (a) and (b) in a proportion of about one part of (a) papaverine hydrochloride to about 1.3 to 20 parts of (b) dimethylaminoethanol acetyl salicylate.

17. Method of claim 15, wherein the active ingredients are (a) and (b) in a proportion of about one part of (a) papaverine hydrochloride to about 1.3 parts of (b) dimethylaminoethanol acetyl salicylate.

18. Method of claim 15, wherein the active ingredients are (a) and (b) in a proportion of about one part of (a) papaverine hydrochloride to about 20 parts of (b) dimethylaminoethanol acetyl salicylate.

* * * * *